(12) United States Patent
Bong et al.

(10) Patent No.: US 11,497,704 B2
(45) Date of Patent: Nov. 15, 2022

(54) AGENT FOR FORMING FILM ON SKIN

(71) Applicant: LG HOUSEHOLD & HEALTH CARE LTD., Seoul (KR)

(72) Inventors: Hyo-Jin Bong, Seoul (KR); Ki-Young Kim, Seoul (KR); Nae-Gyu Kang, Seoul (KR); No-Jin Park, Seoul (KR); Woo-Sun Shim, Seoul (KR); Hyeong-Jin Cho, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 58 days.

(21) Appl. No.: 16/978,917

(22) PCT Filed: Jan. 4, 2019

(86) PCT No.: PCT/KR2019/000169
§ 371 (c)(1),
(2) Date: Sep. 8, 2020

(87) PCT Pub. No.: WO2019/172517
PCT Pub. Date: Sep. 12, 2019

(65) Prior Publication Data
US 2021/0361556 A1    Nov. 25, 2021

(30) Foreign Application Priority Data
Mar. 9, 2018    (KR) .................. 10-2018-0028177

(51) Int. Cl.
*A61K 8/892*    (2006.01)
*A61K 8/19*    (2006.01)
(Continued)

(52) U.S. Cl.
CPC .............. *A61K 8/892* (2013.01); *A61K 8/19* (2013.01); *A61K 8/25* (2013.01); *A61K 8/26* (2013.01);
(Continued)

(58) Field of Classification Search
None
See application file for complete search history.

(56) References Cited

U.S. PATENT DOCUMENTS 6,432,451 B1    8/2002 Lee et al.
9,445,984 B2    9/2016 Mateu et al.
(Continued)

FOREIGN PATENT DOCUMENTS

CN    101627960 A    1/2010
KR    10-2000-0067126 A    11/2000
(Continued)

OTHER PUBLICATIONS

International Search Report issued in PCT/KR2019/000169 (PCT/ISA/210), dated Apr. 18, 2019.

*Primary Examiner* — Nicole P Babson
(74) *Attorney, Agent, or Firm* — Birch, Stewart, Kolasch & Birch, LLP (57) ABSTRACT

The present disclosure relates to a skin film forming agent, and provides a skin film forming agent which comprises dimethiconol, hydride dimethicone and a cross-linking component, and thereby provides a skin film forming agent which has no problem of safety, and forms a film with high intensity, and thereby can solve peeling and slipping of the film and effectively improve skin disadvantages, particularly, wrinkles and elasticity.

25 Claims, 2 Drawing Sheets

(51) Int. Cl.
*A61K 8/25* (2006.01)
*A61K 8/26* (2006.01)
*A61K 8/27* (2006.01)
*A61K 8/29* (2006.01)
*A61K 8/58* (2006.01)
*A61K 8/891* (2006.01)
*A61K 8/96* (2006.01)
*A61Q 1/02* (2006.01)
*A61Q 19/00* (2006.01)
*A61Q 19/08* (2006.01)

(52) U.S. Cl.
CPC .................. *A61K 8/27* (2013.01); *A61K 8/29* (2013.01); *A61K 8/585* (2013.01); *A61K 8/891* (2013.01); *A61K 8/965* (2013.01); *A61Q 1/02* (2013.01); *A61Q 19/007* (2013.01); *A61Q 19/08* (2013.01); *A61K 2800/43* (2013.01); *A61K 2800/612* (2013.01); *A61K 2800/651* (2013.01); *A61K 2800/882* (2013.01); *A61K 2800/95* (2013.01)

(56) References Cited

U.S. PATENT DOCUMENTS

2016/0143840 A1\* 5/2016 Yu ........................... A61P 17/00
 514/772.3
2018/0256636 A1 9/2018 Yu et al.

FOREIGN PATENT DOCUMENTS

| KR | 10-2000-0077183 A | 12/2000 |
| KR | 10-2013-0135843 A | 12/2013 |
| WO | WO 2007/071886 A2 | 6/2007 |
| WO | WO 2010/081886 A2 | 7/2010 |
| WO | WO 2011/143131 A1 | 11/2011 |
| WO | WO 2014/101703 A1 | 7/2014 |

\* cited by examiner

AGENT FOR FORMING FILM ON SKIN

TECHNICAL FIELD

The present application claims the priority based on Korean Patent Application No. 10-2018-0028177 filed on Mar. 9, 2018, and the entire contents disclosed in the description and drawings of the corresponding application are incorporated in the present application.

The present disclosure relates to a skin film forming agent.

BACKGROUND ART

To reduce various skin defects or disadvantages, for example, wrinkles, pigmentation, age spots, skin pore increase, scar, elasticity reduction, sagging, moisture reduction and glow reduction, and improve skin, very various functional components have been reported.

The skin improvement by a physiological approach through these functional components takes a long time and has a disadvantage in that it is difficult to mix them enough to produce a satisfactory effect due to safety and stability problems, and thus it is a difficult problem for consumers to experience quickly. Accordingly, there is an attempt to cover skin disadvantages using filming-forming cosmetics and improve skin defects, particularly, wrinkles and elasticity rapidly, using physical tension. The use of this filming agent utilizes a property that the film is contracted in the drying process during film formation, and is based on the idea that by the contraction, fine wrinkles of skin are pulled and the feeling of tightness is increased, and thereby the fine wrinkles are temporarily removed. As such a filming agent, polysaccharides, polyvinylpyrrolidone (PVP), polyvinyl alcohol (PVA), silicone filming agents, polyurethane materials, and the like may be applied, but in particular, silicone-based filming agents must be an easily accessible filming agent in that it can exhibit properties similar to those of skin, so there is no foreign body sensation and the properties can be easily controlled.

However, when using a filming agent with a strong contracting power, there are problems in that the effect of improving skin disadvantages is very low and the usability and sense of use are bad, for example, that adhesion to skin is weakened and it becomes easy to peel off undesirably for elasticity of skin, and also, there is incompatibility during use due to the hard film, and the film is destroyed in a short time and the film is shiny. In addition, even if a filming agent which has strong contraction and forms a hard film is used, the lasting effect is reduced or there is only a feeling of tightness, but it is difficult to actually feel it.

Recently, a technology for a filming agent which can improve wrinkles and elasticity by the method of forming a film on skin by reacting at a room temperature (Korean Patent Publication No. 10-2017-0063526) has been reported. This applies a polysaccharide polymer grafted with a (met)acrylate group combined with a photoactive compound to skin and exposes it to light radiation to form a film on skin, thereby improving a tension effect. However, the above method cannot be free from safety problems because skin must be irradiated with light.

On the other hand, Korean Patent Publication No. 10-2013-0135843 reported an agent which can improve wrinkles and correct body immediately by forming a film by cross-linking of vinyl dimethicone which is used as a reaction enhancing component and hydride dimethicone which is used as a cross-linking component, but there is a disadvantage in that the film is easily peeled off due to slipping when applied to skin, and therefore it is difficult to last for a long time.

Accordingly, to solve peeling and slipping of the film, without the safety problem which is a disadvantage of the aforementioned skin filming agent, it is solved by applying a film forming agent capable of forming a film with high film intensity, and at the same time, a film forming agent effective in skin disadvantages, particularly, wrinkles and elasticity improvement is to be suggested.

DISCLOSURE

Technical Problem

The present disclosure is to provide a skin film forming agent which has no problem of safety, and forms a film with high intensity to solve peeling and slipping of the film, and effectively improves skin disadvantages, particularly, wrinkles and elasticity.

Technical Solution

To achieve the aforementioned object, the present disclosure provides a skin film forming agent comprising dimethiconol, hydride dimethicone and a cross-linking component.

The skin film forming agent according to one aspect of the present disclosure is characterized in that the dimethiconol and hydride dimethicone are spatially separated from the cross-linking component prior to skin application to prevent contact.

The skin film forming agent according to one aspect of the present disclosure is characterized in that it consists of i) a first agent comprising the dimethiconol and hydride dimethicone, and ii) a second agent comprising the cross-linking agent, and the first agent and the second agent are mixed immediately before skin application and are applied to skin.

The dimethiconol of the skin film forming agent according to one aspect of the present disclosure has the viscosity of 1000 to 100000 cP or cSt, and the hydride dimethicone has the viscosity of 0.1 to 1000 cP or cSt.

The skin film forming agent according to one aspect of the present disclosure comprises 0.1 to 30% (w/w) dimethiconol and 0.1 to 15% (w/w) hydride dimethicone based on the total weight of the skin film forming agent.

The skin film forming agent according to one aspect of the present disclosure has the content of dimethiconol:hydride dimethicone of 1 to 4:1.

The hydride dimethicone of the skin film forming agent according to one aspect of the present disclosure has at least one hydride end.

The SiH content of the hydride dimethicone of the skin film forming agent according to one aspect of the present disclosure is 1 to 15 mmol/g.

The cross-linking component of the skin film forming agent according to one aspect of the present disclosure catalyzes original position cross-linking reaction of dimethiconol and hydride dimethicone.

The skin film forming agent according to one aspect of the present disclosure comprises the cross-linking component of 0.1 to 5% (w/w) based on the total weight of the skin film forming agent.

The cross-linking component of the skin film forming agent according to one aspect of the present disclosure is a platinum catalyst.

The platinum catalyst of the skin film forming agent according to one aspect of the present disclosure is selected from the group consisting of platinum carbonyl cyclovinylmethylsiloxane complex, platinum divinyltetramethyldisiloxane complex, platinum cyclovinylmethylsiloxane complex, platinum octanealdehyde/octanol complex and combinations thereof.

The skin film forming agent according to one aspect of the present disclosure further comprises at least one selected from the group consisting of surface treated mica, zinc oxide, titanium dioxide, aluminum oxide, clay and silica.

The silica of the skin film forming agent according to one aspect of the present disclosure is surface treated with hexamethyldisilazane.

The skin film forming agent according to one aspect of the present disclosure prevents skin wrinkles and laxity, delays skin wrinkles and laxity, improves skin wrinkles and laxity, enhances skin elasticity, provides skin moisture, and provides skin vitality.

Advantageous Effects

The present disclosure provides a skin film forming agent which has no problem of safety, and forms a film with high intensity to solve peeling and slipping of the film, and effectively improves skin disadvantages, particularly, wrinkles and elasticity.

MODE FOR INVENTION

The present disclosure to achieve the aforementioned object is characterized by a skin film forming agent comprising dimethiconol, hydride dimethicone and a cross-linking component. Hereinafter, the present disclosure will be specifically described in reference to drawings.

The present disclosure provides a skin film forming agent comprising dimethiconol, hydride dimethicone and a cross-linking component.

The term of the present disclosure, "skin film forming agent" is an agent which forms a film improving skin defects on skin, and includes a cosmetic agent.

The dimethiconol is dimethylsiloxane having a hydroxyl group as an end, and as one example, it may have the structure of the following chemical formula.

[Chemical formula 1]

In the formula, n may be 450 to 3000, preferably, 500 to 2750, more preferably, 550 to 2500. In addition, a hydroxy group or a hydride group may be not present in the middle, and it may be present at both ends of the polymer.

The dimethiconol is a polymer having a molecular weight of about 26000 to 175000 Da or less, and specifically, it may be 29000 to 160000 Da, more specifically, 32000 to 145000 Da.

The hydride dimethicone is polysiloxane having a hydrogen as an end, and as one example, it may have the structure of the following chemical formula.

[Chemical formula 2]

In the formula, m may be 0 to 400, and n may be 0 to 35, and preferably, m may be 0 to 300, and n may be 0 to 30, and more preferably, m may be 0 to 300, and n may be 0 to 25.

The hydride dimethicone is a polymer having a molecular weight of about 200 to 30000 Da, and specifically, it may be 300 to 25000 Da, more specifically, 400 to 20000 Da.

According to one aspect of the present disclosure, the dimethiconol and hydride dimethicone may be spatially separated from the cross-linking component prior to skin application to prevent contact.

The term of the present disclosure, "cross-linking component" is a component which induces original position formation between dimethiconol and hydride dimethicone, and thereby, it causes condensation of these elements so that the film is formed on skin.

According to one aspect of the present disclosure, the skin film forming agent of the present disclosure may consist of i) a first agent comprising the dimethiconol and hydride dimethicone, and ii) a second agent comprising the cross-linking agent, and the first agent and the second agent may be mixed immediately before skin application and may be applied to skin. In other words, the dimethiconol and hydride dimethicone forming the film structure of the present disclosure and the cross-linking component catalyzing their reaction are spatially separated before use to prevent contact. The dimethiconol and hydride dimethicone and the cross-linking component may prevent contact prior to use by common means known to those skilled in the art. According to one example, the first agent comprising dimethiconol and hydride dimethicone and the second agent comprising the cross-linking component are two parts of agents which are packaged in separated container and are mixed before use. As another example, the first agent comprising dimethiconol and hydride dimethicone is applied and the second agent comprising the cross-linking agent is applied on the first agent. As other example, the second agent comprising the cross-linking component is applied to skin firstly, and the first agent comprising dimethiconol and hydride dimethicone is applied on the second agent. As other example, the first agent comprising dimethiconol and hydride dimethicone and the second agent comprising the cross-linking component are packaged in the same container together and are mixed when the components come out of the container.

The term of the present description, "viscosity" represents a measurement of resistance of a fluid in which modification occurs by one of shear stress or tensile stress. The viscosity may be expressed as a dynamic viscosity (absolute viscosity, common unit Pa·s, Poise, P, cP) or kinematic viscosity (common unit cm$^2$/s, Stokes, St, cSt) that is a value of the common unit dynamic viscosity divided by density. Therefore, when the density of the fluid is about 1, the dynamic viscosity and kinematic viscosity are almost equivalent. Those skilled in the art can understand that the viscosity may be modified depending on the temperature and pressure, and such a measurement value can be appropriately adjusted. Without undue experimentation, those skilled in the art may determine how to measure the viscosity of a fluid, for example, using a viscometer or rheometer. Representatively, a capillary viscometer, a rotation viscometer or a rheometer for measuring the viscosity in a specific deformation device, and as one example, a value obtained after measuring about 1 minute after setting to Speed 30 RPM at 25° C. using a viscometer (BROOKFIELD, Inc.) is used as the viscosity.

According to one aspect of the present disclosure, the dimethiconol may have a viscosity of 1000 to 100000 cP or cSt, preferably, 10000 to 90000 cP or cSt, more preferably, 20000 to 80000 cP or cSt (25° C.).

According to one aspect of the present disclosure, the dimethiconol having a certain viscosity may be provided by

According to one aspect of the present disclosure, the skin film forming agent of the present disclosure may have the content of dimethiconol:hydride dimethicone of 1 to 4:1, specifically, 2 to 3:1.

According to one aspect of the present disclosure, the hydride dimethicone may have at least one hydride end. As one example, it may have two hydride groups at both ends and have 0 to 20, specifically, 0 to 12, more specifically, 0 to 8 Si—H units in a monomer unit.

According to one aspect of the present disclosure, the SiH content of hydride dimethicone may be 1 to 15 mmole/g, specifically, 2 to 12 mmole/g, more specifically, 4 to 10 mmole/g, most specifically, 6 to 9 mmole/g.

According to one aspect of the present disclosure, the cross-linking component of the skin film forming agent of the present disclosure may catalyze original position cross-linking reaction of dimethiconol and hydride dimethicone. In other words, the hydroxyl group end of dimethiconol and the hydrogen end of hydride dimethicone are combined to form hydrogen while forming a film (See the following reaction formula).

[Reaction formula]

consisting of only dimethiconol with an appropriate molecular weight having the same viscosity as the final viscosity, or appropriately mixing high-viscosity dimethiconol with a high molecular weight and low-viscosity dimethiconol with a low molecular weight.

The hydride dimethicone may have a viscosity of 0.1 to 1000 cP or cSt, preferably, 0.5 to 800 cP or cSt, more preferably, 1 to 600 cP or cSt (25° C.).

According to one aspect of the present disclosure, the hydride dimethicone having a certain viscosity may be provided by consisting of only hydride dimethicone with an appropriate molecular weight having the same viscosity as the final viscosity, or appropriately mixing high-viscosity hydride dimethicone with a high molecular weight and low-viscosity hydride dimethicone with a low molecular weight.

According to one aspect of the present disclosure, the content of dimethiconol may be 0.1 to 30% (w/w), specifically, 5 to 25% (w/w), more specifically, 10 to 20% (w/w), based on the total weight of the skin film forming agent. As one example, the content of dimethicone in the skin film forming agent is 15% (w/w).

According to one aspect of the present disclosure, the content of hydride dimethicone may be 0.1 to 15% (w/w), specifically, 3 to 12% (w/w), more specifically, 5 to 10% (w/w), based on the skin film forming agent. As one example, the content of dimethicone in the skin film forming agent is 7% (w/w).

In particular, the conventional film formation by binding of vinyl silicone and hydride dimethicone have no by-products produced by reaction and therefore there is little degree of contraction of the film, and thus it has been widely used as a material for modeling teeth. On the other hand, the reaction by the present disclosure is effective in wrinkle and elasticity improvement, as the contraction during the film formation is high by reaction producing hydrogen in the process of forming the film, and also the film with high strength is formed. In addition, the hydroxyl functional group at the dimethiconol end acts as an element which enhances adhesion by hydrogen bonds with keratin of the skin stratum corneum, and is firmly fixed without slipping after skin application to increase water resistance and durability.

According to one aspect of the present disclosure, the content of the cross-linking component may be 0.1 to 5% (w/w), specifically, 0.2 to 3% (w/w), more specifically, 0.5 to 2% (w/w), based on the skin film forming agent.

According to one aspect of the present disclosure, the cross-linking component of the skin film forming agent may be a metal catalyst, specifically, a platinum catalyst, and more specifically, may be selected from the group consisting of platinum carbonyl cyclovinylmethylsiloxane complex, platinum divinyltetramethyldisiloxane complex, platinum cyclovinylmethylsiloxane complex, platinum octanealdehyde/octanol complex and combinations thereof.

According to one aspect of the present disclosure, the skin film forming agent may further comprise a reinforcing agent component to provide preferable characteristics to the film. As the reinforcing agent which can be used in the present disclosure, it may further comprise at least one selected from the group consisting of surface treated mica, zinc oxide, titanium dioxide, aluminum oxide, clay and silica. As one example, the silica may be fumed silica, and the fumed silica may be surface treated with hexamethyldisilazane. The reinforcing agent component may have a surface area of about 50 to about 400 m$^2$/g, specifically, about 110 to about 330 m$^2$/g, more specifically, about 170 to about 270 m$^2$/g. In one aspect, the reinforcing component has a surface area of about 220±25 m$^2$/g. As one example, the reinforcing agent component has a mean particle size of about 1 to about 500 nm.

According to one aspect of the present disclosure, the skin film forming agent of the present disclosure may further comprise at least one selected from the group consisting of a touch modifying agent, spreadability enhancer, attachment modifying agent, diluent, adhesion modifying agent, optical modifying agent, particle, volatile siloxane, emulsifier, safener, surfactant, thickener, solvent, film forming agent, wetting agent, preservative and pigment.

According to one aspect of the present disclosure, the skin film forming agent of the present disclosure may conceal, alleviate, improve or inhibit various skin defects.

The term of the present disclosure, "skin defects" include dark red birthmarks or nevus flammeus (e.g., nape nevus flammeus or midline nevus flammeus), freckles, wrinkles, blemishes, acne, spots, scars, tattoos, bruising, skin damage, birthmarks, sunlight damage, aging damage, non-uniform skin tone, saggy skin, skin roughness, hyperpigmentation, enlarged pores, telangiectasia, rubefaction, gloss, cellulite, gestational glands or loss of skin elasticity.

According to one aspect of the present disclosure, the skin film forming agent of the present disclosure may conceal (cover), alleviate, improve or inhibit at least one skin defects selected from wrinkles, pigmentation, age spots, skin pore increase, scar, elasticity reduction, sagging, moisture reduction and gloss reduction of skin.

According to one aspect of the present disclosure, the skin film forming agent of the present disclosure may form a film on skin to protect the skin from external stimulus.

According to one aspect of the present disclosure, the skin film forming agent of the present disclosure may be provided as a common cosmetic formulation. As one example, it may be a formulation of liquid, gel, foam, spray, mousse, ointment, cream, emulsion, suspension, lotion, milk, solid paste or semi-solid paste.

Hereinafter, the present disclosure will be described in more detail by examples. However, these are intended to illustrate the present disclosure in more detail only, but the scope of the present disclosure is not limited thereto.

1. Preparation of Comparative Example 1

1) First Agent of Comparative Example 1 (Silicone Agent)

Components 1~3 of the following table were mixed until they were evenly mixed well at 1,000 rpm. After adding components 5~6 in order to make it homogeneous, component 4 was slowly added and they are mixed until no particles were visible (mixture A). After mixing components 7~8 in another container, it was slowly added to mixture A and mixed to be mixed evenly to complete it.

TABLE 1

| Classification | Raw material name | Content (%) |
| --- | --- | --- |
| 1 | Vinyl Dimethicone (165,000 cP) (Andisil ® VS 165,000) | 3.43 |
| 2 | Vinyl Dimethicone (10,000 cSt) (Andisil ® VS 10,000) | 14.61 |
| 3 | Hydride Dimethicone (45 cSt) (Andisil ® XL-11) | 7.16 |
| 4 | Surface treated silica (Aerosil R8200) | 6.8 |
| 5 | Cyclopentasiloxane | 12.0 |
| 6 | Dimethicone/PEG-10/15 Crosspolymer | 4.0 |
| 7 | Purified water | Fill to 100 |
| 8 | 1,2-Hexanediol | 1.5 |

2) Second Agent of Comparative Example 1 (Catalyst Agent)

Components 1~3 of the following table were stirred at 1,000 rpm enough and mixed (mixture B), and while slowly adding the solution in which components 4~7 were mixed in other container to mixture B, it was mixed at 2,000 rpm with a homomixer. Finally, component 8 was added to complete the formulation.

TABLE 2

| Classification | Raw material name | Content (%) |
| --- | --- | --- |
| 1 | Dimethicone crosspolymer | 10.0 |
| 2 | Dimethicone/PEG-10/15 Crosspolymer | 4.0 |
| 3 | Cyclopentasiloxane | 15.8 |
| 4 | Purified water | 63.2 |
| 5 | Sodium chloride | 0.5 |
| 6 | 1,2-Hexanediol | 1.5 |
| 7 | Glycerin | 4.0 |
| 8 | Karstedt platinum catalyst (solution 2% platinum) | 1.0 |

2. Preparation of Example 1

1) First Agent of Example 1 (Silicone Agent)

Components 1~2 of the following table were mixed until they were evenly mixed well at 1,000 rpm. After adding components 4~5 in order to make it homogeneous, component 3 was slowly added and they are mixed until no particles were visible (mixture C). After mixing components 6~7 in other container, it was slowly added to mixture C and mixed to be mixed evenly to complete it.

TABLE 3

| Classification | Raw material name | Content (%) |
| --- | --- | --- |
| 1 | Dimethiconol (20,000 cP) (Andisil ® OH 20,000) | 15.0 |
| 2 | Hydride Dimethicone (45 cSt) (Andisil ® X-10) | 7.0 |
| 3 | Surface treated silica (Aerosil R8200) | 3.4 |
| 4 | Cyclopentasiloxane | 18.0 |
| 5 | Dimethicone/PEG-10/15 Crosspolymer | 5.0 |
| 6 | Purified water | Fill to 100 |
| 7 | 1,2-Hexanediol | 1.5 |

2) Second Agent of Example 1 (Catalyst Agent)

Components 1~3 of the following table were stirred at 1,000 rpm enough and mixed (mixture D), and while slowly adding the solution in which components 4~7 were mixed in other container to mixture D, it was mixed at 2,000 rpm with a homomixer. Finally, component 8 was added to complete the formulation.

TABLE 4

| Classification | Raw material name | Content (%) |
| --- | --- | --- |
| 1 | Dimethicone crosspolymer | 10.0 |
| 2 | Dimethicone/PEG-10/15 Crosspolymer | 4.0 |
| 3 | Cyclopentasiloxane | 15.8 |
| 4 | Purified water | 63.2 |
| 5 | Sodium chloride | 0.5 |
| 6 | 1,2-Hexanediol | 0.5 |
| 7 | Glycerin | 4.0 |
| 8 | Karstedt platinum catalyst (solution 2% platinum) | 1.0 |

3. Visual Evaluation of Wrinkle Improvement

For the same subject, Comparative example 1 and Example 1 prepared above were applied and then the phenomenon of wrinkle improvement over time was confirmed. Specifically, each of the first agent and the second agent of Comparative example 1 and Example 1 prepared above was mixed 1:1 and applied.

Figure 1:
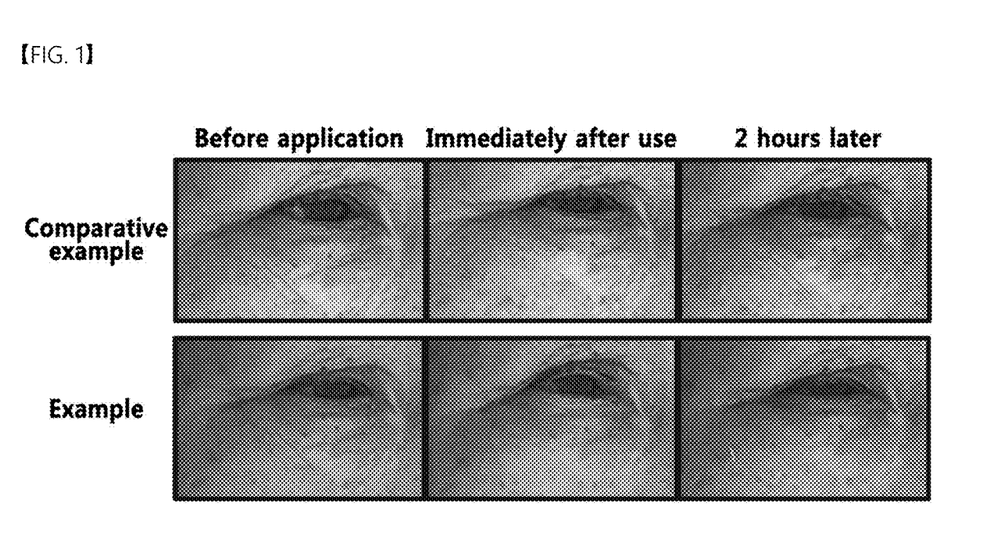
FIG. 1 is the result of evaluating the improvement of wrinkles of the skin film forming agent according to one example of the present disclosure with naked eyes.

The confirmation result was shown in FIG. 1, and it can be confirmed that the effect of wrinkle improvement of the example was doubled.

4. Effect of Improving Slipping

Comparative example 1 and Example 1 prepared above were applied to skin and then it was rubbed with fingers 10 times to confirm the phenomenon of slipping of the film.

Figure 2:
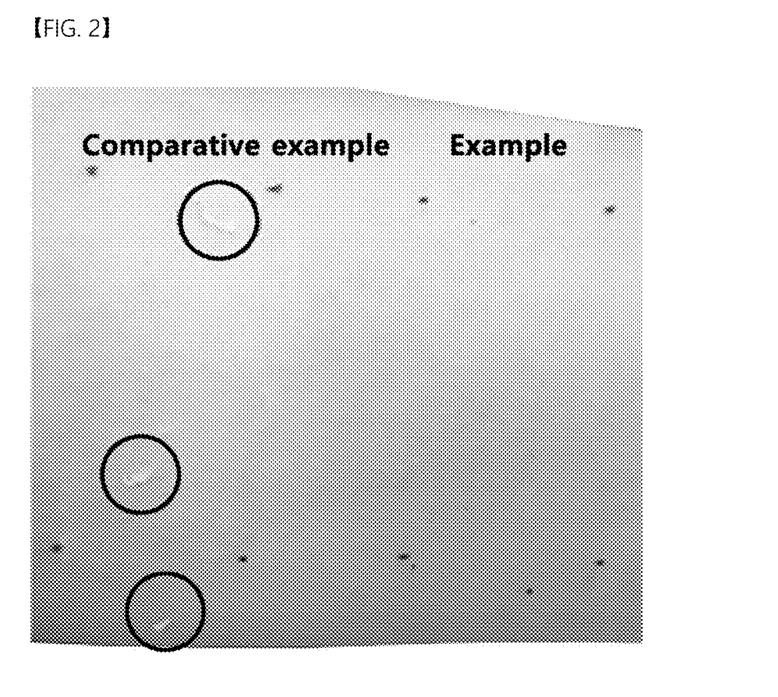
FIG. 2 is the result of confirming the improvement of slipping of the skin film forming agent according to one example of the present disclosure.

The confirmation result was shown in FIG. 2, and it can be confirmed that example was attached on skin without slipping.

5. Determination of Effect of Improving Filming Agent

To determine physical properties of the filming agent, for the formulations prepared by the compositions suggested in the following table, the strength and elongation were measured. The strength of the film is the strength when the specimen breaks during the tensile test, and the elongation is the length of the film stretching until it breaks.

TABLE 5

| Raw material name | Experiment 1 | Experiment 2 | Experiment 3 | Experiment 4 | Experiment 5 | Experiment 6 |
| --- | --- | --- | --- | --- | --- | --- |
| Vinyl dimethicone (1,000 cSt) (Andisil ® VS 1,000) | 6.00 g | — | — | — | — | — |
| Vinyl dimethicone (10,000 cSt) (Andisil ® VS 10,000) | — | 6.00 g | — | — | — | — |
| Vinyl dimethicone (65,000 cP) (Andisil ® VS 65,000) | — | — | 6.00 g | — | — | — |
| Dimethiconol (2,000 cP) (Andisil ® OH 2,000) | — | — | — | 6.00 g | — | — |
| Dimethiconol (20,000 cP) (Andisil ® OH 20,000) | — | — | — | — | 6.00 g | — |
| Dimethiconol (80,000 cP) (Andisil ® OH 80,000) | — | — | — | — | — | 6.00 g |
| Hydride dimethicone (45 cSt) (Andisil ® XL 10) | 2.15 g | 2.15 g | 2.15 g | 2.15 g | 2.15 g | 2.15 g |

The experiments were progressed in accordance with ASTM D638 standard. The repeated test was repeated at a rate of 10 mm/s 15 times, and the tensile test was progressed at a rate of 10 mm/s. The experimental result was shown in the following table and FIG. 3.

TABLE 6

| | Experiment 1 | Experiment 2 | Experiment 3 | Experiment 4 | Experiment 5 | Experiment 6 |
| --- | --- | --- | --- | --- | --- | --- |
| Strength (kPa) | 796.2 | 876.0 | 904.4 | 360.9 | 1467.7 | 3329.9 |
| Elongation (%) | 150.7 | 350.0 | 446.1 | 116.2 | 558.9 | 672.0 |

Figure 3:
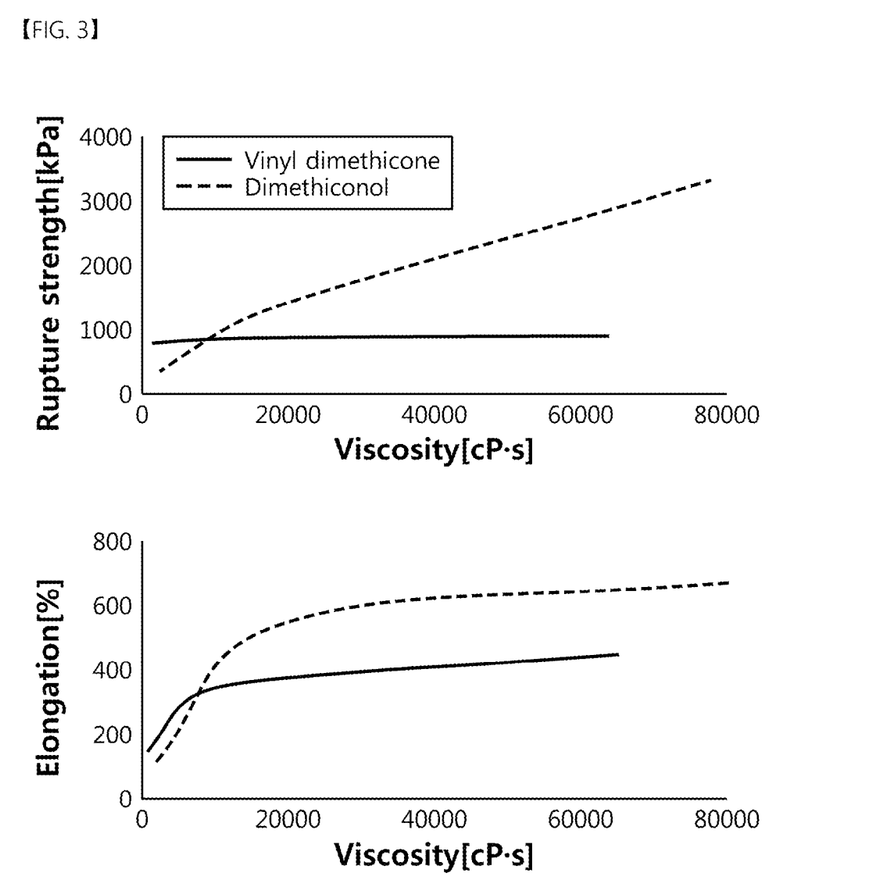
FIG. 3 is the result of measuring the rupture strength and elongation of the skin film forming agent according to one example of the present disclosure.

Therefore, it was confirmed that the rupture strength and elongation, and the like of the experiments 4, 5 and 6 using dimethiconol were improved than the experiments 1, 2 and 3 using vinyl dimethicone, and in particular, when the viscosity of dimethiconol was 20,000 cP or more, both the rupture strength and elongation were excellent than vinyl dimethicone.

6. Panel Evaluation for Wrinkle and Elasticity Improvement

1) Preparation of Skin Film Forming Agent

The first agent (silicone agent) of each Example and Comparative example was prepared by the compositions of the following table.

TABLE 7

| Classificaton | Raw material name | Example 2 | Example 3 | Example 4 | Example 5 | Comparative example 2 | Comparative example 3 |
|---|---|---|---|---|---|---|---|
| 1 | Dimethiconol (2,000 cP) (Andisil ® OH 2,000) | 15.0 | — | — | — | — | — |
| 2 | Dimethiconol (20,000 cP) (Andisil ® OH 20,000) | — | 15.0 | — | 7.5 | — | — |
| 3 | Dimethiconol (80,000 cP) (Andisil ® OH 80,000) | — | — | 15.0 | 7.5 | — | — |
| 4 | Vinyl dimethicone (1000 cSt) (Andisil ® VS1000) | — | — | — | — | 15.0 | 15.0 |
| 5 | Hydride dimethicone (Andisil ® XL-11) (45 cSt, SiH content = 4.85 mmol/g) | — | — | — | — | 7.0 | — |
| 6 | Hydride dimethicone (Andisil ® XL-10) (45 cSt, SiH content = 7.35 mmol/g) | 7.0 | 7.0 | 7.0 | 7.0 | — | 7.0 |
| 7 | Surface treated silica (Aerosil R8212S) | 3.4 | 3.4 | 3.4 | 3.4 | 3.4 | 3.4 |
| 8 | Cyclopentasiloxane | 18.0 | 18.0 | 18.0 | 18.0 | 18.0 | 18.0 |
| 9 | Dimethicone/PEG-10/15 Crosspolymer | 5.0 | 5.0 | 5.0 | 5.0 | 5.0 | 5.0 |
| 10 | Purified water | Fill to 100 | Fill to 100 | Fill to 100 | Fill to 100 | Fill to 100 | Fill to 100 |
| 11 | 1,2-Hexanediol | 1.5 | 1.5 | 1.5 | 1.5 | 1.5 | 1.5 |

The second agent (catalyst agent) of each Example and Comparative example was prepared by the compositions of the following table.

TABLE 8

| Classification | Raw material name | Content (%) |
|---|---|---|
| 1 | Dimethicone crosspolymer | 10.0 |
| 2 | Dimethicone/PEG-10/15 Crosspolymer | 4.0 |
| 3 | Vinyl dimethicone (1000 cSt) (Andisil ® VS1000) | 5.0 |
| 4 | Cyclopentasiloxane | 10.8 |
| 5 | Purified water | 64.2 |
| 6 | Sodium chloride | 0.5 |
| 7 | 1,2-Hexanediol | 0.5 |
| 8 | Glycerin | 4.0 |
| 9 | Karstedt platinum catalyst (solution 2% platinum) | 1.0 |

2) Evaluation Result

The test was conducted for 10 professional panelists, and each item was evaluated on a scale of 1~5 based on a perfect score of 5. The evaluation result was described in the following table.

TABLE 9

| | Example 2 | Example 3 | Example 4 | Example 5 | Comparative example 2 | Comparative example 3 |
|---|---|---|---|---|---|---|
| Film formation | 2.53 | 3.50 | 4.63 | 4.37 | 2.35 | 2.40 |
| Wrinkle improvement | 2.83 | 3.61 | 4.31 | 4.02 | 2.66 | 2.54 |
| Slipping | 4.20 | 4.31 | 4.45 | 4.41 | 3.01 | 3.33 |
| Durability | 3.62 | 3.55 | 3.81 | 3.77 | 2.57 | 2.75 |

As the experimental result, in all the evaluated items, all the Examples 2 to 5 using dimethiconol showed an excellent effect compared to Comparative example 2 and Comparative example 3 using vinyl dimethicone. Overall, the higher the viscosity of dimethiconol was, the film formation, wrinkle improvement, slipping and durability were increased, and all the Examples 2 to 5 showed the higher result in all the items compared to all the Comparative examples 2 and 3. Specifically, in case of film formation, it can be seen that Example 4 was 97% higher than Comparative example 2, and in case of wrinkle improvement, Example 4 was 69.7% higher than Comparative example 3, and in case of slipping and durability, all the examples were 38% higher than Comparative example 2.

In the above, the applicant has described preferable examples of the present disclosure, but these examples are only one example which implements the technical spirit of the present disclosure, and any modification or alteration should be interpreted as belonging to the scope of the present disclosure as long as it implements the technical spirit of the present disclosure.

INDUSTRIAL APPLICABILITY

The present disclosure provides a skin film forming agent which has no problem of safety, and forms a film with high intensity, and thereby can solve peeling and slipping of the film and effectively improve skin disadvantages, particularly, wrinkles and elasticity, and thereby it can be used as a composition for skin in various formulations containing the same.

The invention claimed is:

1. A skin film forming agent comprising dimethiconol, hydride dimethicone and a cross-linking component,
wherein the skin film forming agent comprises 5 to 25% (w/w) of dimethiconol and 0.1 to 15% (w/w) of hydride dimethicone based on the total weight of the skin film forming agent, and
wherein the dimethiconol has a viscosity of 10,000 to 100,000 cP or cSt at 25° C.

2. The skin film forming agent according to claim 1, wherein the dimethiconol and hydride dimethicone are spatially separated from the cross-linking component prior to skin application to prevent contact.

3. The skin film forming agent according to claim 1, wherein the skin film forming agent consists of i) a first agent comprising the dimethiconol and hydride dimethicone, and ii) a second agent comprising the cross-linking agent, and the first agent and the second agent are mixed just before skin application and then are applied to skin.

4. The skin film forming agent according to claim 1, wherein the hydride dimethicone has a viscosity of 0.1 to 1000 cP or cSt at 25° C.

5. The skin film forming agent according to claim 1, wherein an amount ratio of dimethiconol:hydride dimethicone is 1:1 to 4:1.

6. The skin film forming agent according to claim 1, wherein the hydride dimethicone has at least one hydride end.

7. The skin film forming agent according to claim 1, wherein the hydride dimethicone has a SiH content of 1 to 15 mmol/g.

8. The skin film forming agent according to claim 1, wherein the cross-linking component catalyzes original position cross-linking reaction of dimethiconol and hydride dimethicone.

9. The skin film forming agent according to claim 1, wherein the skin film forming agent comprises 0.1 to 5% (w/w) of the cross-linking component based on the total weight of the skin film forming agent.

10. The skin film forming agent according to claim 9, wherein the cross-linking component is a platinum catalyst.

11. The skin film forming agent according to claim 10, wherein the platinum catalyst is selected from the group consisting of platinum carbonyl cyclovinylmethylsiloxane complex, platinum divinyltetramethyldisiloxane complex, platinum cyclovinylmethylsiloxane complex, platinum octanealdehyde/octanol complex and combinations thereof.

12. The skin film forming agent according to claim 1, wherein the skin film forming agent further comprises at least one selected from the group consisting of surface treated mica, zinc oxide, titanium dioxide, aluminum oxide, clay and silica.

13. The skin film forming agent according to claim 12, wherein the silica is surface treated with hexamethyldisilazane.

14. The skin film forming agent according to claim 1, wherein the skin film forming agent conceals (covers), alleviates, improves or inhibits at least one skin defects selected from wrinkles, pigmentation, age spots, skin pore increase, scar, elasticity reduction, sagging, moisture reduction and gloss reduction of skin.

15. The skin film forming agent according to claim 1, wherein the hydride dimethicone has a viscosity of 0.5 to 800 cP or cSt at 25° C.

16. The skin film forming agent according to claim 1, wherein the hydride dimethicone has a viscosity of 1 to 600 cP or cSt (25° C.).

17. The skin film forming agent according to claim 1, wherein the content of dimethiconol is 10 to 20% (w/w), based on the total weight of the skin film forming agent.

18. The skin film forming agent according to claim 1, wherein the content of hydride dimethicone is 3 to 12% (w/w), based on the total weight of the skin film forming agent.

19. The skin film forming agent according to claim 1, wherein the content of hydride dimethicone is 5 to 10% (w/w), based on the total weight of the skin film forming agent.

20. The skin film forming agent according to claim 1, wherein the skin film forming agent comprises 0.5 to 2% (w/w) of the cross-linking component based on the total weight of the skin film forming agent.

21. The skin film forming agent according to claim 1, wherein the dimethiconol is a dimethylsiloxane polymer having at least one hydroxyl group at the end of the dimethylsiloxane polymer.

22. The skin film forming agent according to claim 1, wherein the dimethiconol comprises a compound of Chemical Formula 1:

[Chemical formula 1]

wherein n is 450 to 3000.

23. The skin film forming agent according to claim 1, wherein the dimethiconol is a polymer having a molecular weight of about 26000 to 175000 Da.

24. The skin film forming agent according to claim 1, wherein the hydride dimethicone comprises a compound of Chemical Formula 2:

[Chemical formula 2]

wherein m is 0 to 400, and n is 0 to 35.

25. The skin film forming agent according to claim 1, wherein the skin film forming agent does not comprise a vinyl terminated organopolysiloxane.

* * * * *